United States Patent [19]

Mazzi et al.

[11] Patent Number: 5,635,158
[45] Date of Patent: Jun. 3, 1997

[54] PEPTIDES MODIFIED BY THE PHOSPHINE GROUP FOR MARKING WITH 99M TC AND 186-188 RE OR PARAMAGNETIC AGENTS

[75] Inventors: Ulderico Mazzi, Verona; Fabio Lunghi, Moncrivello, both of Italy

[73] Assignee: Sorin Radiofarmaci SRL, Milan, Italy

[21] Appl. No.: 494,105

[22] Filed: Jun. 23, 1995

[51] Int. Cl.$^6$ .................... A61K 51/08; A61K 38/00; C07F 9/02; A61B 5/055

[52] U.S. Cl. .................... 424/1.69; 424/1.45; 424/1.65; 424/1.77; 424/9.34; 424/9.36; 424/9.365; 534/10; 534/11; 534/14; 534/16; 534/300; 534/311; 534/323; 568/8; 568/10; 568/17; 564/161; 562/8

[58] Field of Search .................... 424/1.45, 1.77, 424/1.65, 1.69, 9.34, 9.36, 9.365; 534/10, 11, 14, 16; 530/323, 300, 311; 556/13, 15; 568/8, 10, 17; 562/8; 564/161

[56] References Cited

U.S. PATENT DOCUMENTS 5,382,654  1/1995  Lyle et al. .

FOREIGN PATENT DOCUMENTS 527056   2/1993  European Pat. Off. .
9308839  5/1993  WIPO .

OTHER PUBLICATIONS

Santimaria et al., "Preparation and Characterization of a new rhenium(v) complex containing the 3–diphenylphosphino-propinoylglycyl–L–(S–benzl)–cysteinyl methyl ester ligand", Inorganica Chimica Acta, 240, pp. 291–297, 1995.
"Synthesis and Characterization of Technetium and Rhenium Complexes of N,N'-1,2-ethylenediylbis-L-cysteine. Neurolite® and Its Metabolites", pp. 433–444 (Conference Technetium and Rhenium In Chemistry and Nuclear Medicine 3, Cortina International 1989).
"Synthesis and Characterization of Neutral Technetium (III)–99 and –99m Complexes with O,P–Bidentate Phosphinocarboxylate Ligands. Crystal Structure of mer–[Tc(02CCH2CH2PPh2)3].2Me2SO+", (J. Chem. Soc. Dalton Tras., vol. 19, pp. 2901–2908, 1993).
"Neutral Technetium (II)–99m Complexes As Potential Brain Perfusion Imaging Agents", (Nucl. Med. Biol., vol. 14, Nos. 5, 1987, pp. 503–510).

*Primary Examiner*—Gary E. Hollinden
*Assistant Examiner*—Michael G. Hartley
*Attorney, Agent, or Firm*—George P. Hoare, Jr.; Rogers & Wells

[57] ABSTRACT

The peptides described are modified with the phosphine group and are useful for marking with $^{99m}$Tc and $^{186-188}$Re or paramagnetic agents for use in diagnosis and radiotherapy; in particular chelating compounds having the co-ordinating sets $PN_2X$, where X is —S, —O, COO—, $PN_3$, $P_2N_3$ and $P_2N_2$ are described.

17 Claims, No Drawings

PEPTIDES MODIFIED BY THE PHOSPHINE GROUP FOR MARKING WITH 99M TC AND 186-188 RE OR PARAMAGNETIC AGENTS

DESCRIPTION

The present invention relates to the use of molecules containing phosphine groups for marking with $^{99m}Tc$, $^{186-188}Re$ or paramagnetic agents.

The marking of protein or peptide molecules with $^{99m}Tc$ and $^{186-188}Re$ is the future challenge in the field of radiopharmaceuticals both for diagnosis and for radiotherapy.

Quite a number of results relating to the coupling to protein molecules of so-called "chelating agents" which enable the radionuclide to remain firmly bonded thereto are already reported in the literature.

Moreover, in recent years, chelating agents which contain small peptides (for example $MAG_3$) have been studied, that is, it has been established that, in the co-ordinating (chelating) set around the technetium or rhenium, amide groups or other groups belonging to amino-acids such as, for example, —SH, —COOH, —NH$_2$, OH, etc., can contribute to the stabilization of the metal-chelating agent complex.

The study of new tracers for magnetic resonance is also of very great interest. The principle for the design of these new molecules is again that of possessing a useful biological tropism. The difference lies in the tracer which, for magnetic resonance, has to have a highly paramagnetic element. The discovery of these molecules would allow this technique to make a qualitative jump from topology to functional diagnostics.

As a result of the present invention, it has been found that the insertion of the phosphine group in peptides permits the production of molecules which are useful as chelating agents for $^{99m}Tc$, $^{186-188}Re$ or paramagnetic agents, these molecules using, as co-ordinating sets, the phosphine group and adjacent functional groups belonging to the peptide in question.

The subject of the invention is therefore peptide molecules modified with the phosphine group as defined by the structural formulae given below and their use as chelating agents for technetium, rhenium and paramagnetic agents.

In particular, the molecules of the invention conform to the following general structural formula:

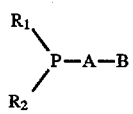
(I)

in which $R_1$ and $R_2$ are selected independently from the group consisting of:

H, linear or branched $C_1$-$C_5$ alkyl, linear or branched substituted $C_1$-$C_5$ alkyl, OH, $C_1$-$C_5$ alkoxy, phenoxy, and substituted phenyl groups, and in which A is alkylene carbonyl or alkylene amino, in which the alkylene has from 1 to 4 carbon atoms and may be linear or branched, and in which, when A is alkylene carbonyl, B is:

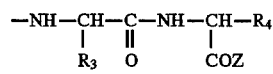

in which $R_3$ is a group selected from the radicals constituting the lateral chain of a natural amino-acid;

$R_4$ is selected from the group consisting of:

H, linear or branched $C_1$-$C_4$ alkyl (preferably methyl, ethyl, isopropyl and 2-methylpropyl) groups, —CH$_2$-C$_6$H$_5$, —(CH$_2$)$_r$NH$_2$ where r is an integer from 1 to 4, —(CH$_2$)$_p$—CONH$_2$, where p is an integer from 1 to 3, —(CH$_2$)$_n$XR$_5$ where n is 1 or 2 and X is selected from —O$^-$, —S$^-$, and —COO$^-$, and $R_5$ is H or a protector group;

Z is OH, OMe, NH$_2$ or is the same as $R_4$, or Z is a peptide with biological properties useful for diagnosis, radiotherapy, or magnetic resonance, bonded to the preceding carbon atom by means of its N-terminal group;

and in which, when A is alkylene amino, B is selected from the group consisting of:

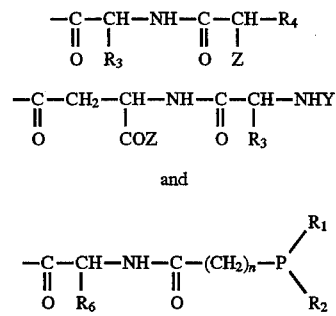

and

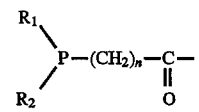

where $R_1$, $R_2$, $R_3$, $R_4$, n and Z have the meanings given above and $R_6$ has the same meaning as $R_3$ given above, or has the meaning of Z given above, and Y is H or $$\begin{array}{c} R_1 \\ \diagdown \\ P-(CH_2)_n-C- \\ \diagup \quad\quad\quad \| \\ R_2 \quad\quad\quad\quad O \end{array}$$

where $R_1$, $R_2$ and n have the meanings given above.

When $R_1$ and $R_2$ in formula (I) are substituted alkyl groups, the substituents are preferably hydroxyl, ether (preferably $C_1$-$C_5$ alkoxy), ester (preferably $C_1$-$C_5$COO—), amide (preferably CO—NH$_2$), ketone (preferably —CO—($C_1$-$C_4$) alkyl), aldehyde (preferably —COH) or nitrile groups. When $R_1$ and $R_2$ in formula (I) are substituted phenyl, the substituents are preferably selected from hydroxyl, ketone, nitrile, ether (—O—$C_1$-$C_5$), ester and amide groups as defined above.

When X is —S$^-$, the protector groups $R_5$ at X are preferably selected from $C_1$-$C_5$ alkyl, phenyl, and substituted benzoyl groups, for example, such as terbutyl, methoxymethyl, 2-tetrahydropyranyl, benzyl, 3,4-dimethylbenzyl, p-methoxybenzyl, p-hydroxy-o-acetoxybenzyl, benzylthiomethyl, p-nitrobenzyl, diphenylmethyl, bis (4-methoxyphenyl)methyl, phenyl, 2,4-dinitrophenyl, acetylbenzoyl, thiobenzoyl, butoxycarbonyl, benzyloxycarbonyl, and N-methoxymethyl groups;

when X is COO$^-$, $R_5$ is preferably a linear or branched $C_1$-$C_5$ alkyl group or a $C_1$-$C_5$ alkyl group substituted with $C_1$-$C_5$ alkylester or arylester groups;

when X is O$^-$, $R_5$ is preferably a $C_1$-$C_5$ alkyl group, an aryl group or a $C_1$-$C_5$ alkylcarbonyl or arylcarbonyl group such as, for example, an acetyl, phenyl, benzyl, terbutyl, methyl, benzyloxycarbonyl, BOC, 1-benzyloxycarbonylamino-2,2,2-trifluoroacetyl, or o-trialkylsilyl group.

When Z is a molecule with biological properties useful for diagnosis, radiotherapy or magnetic resonance, it is selected, for example, from avidin, biotin, low-density lipoprotein (LDL), chemotactic peptides for having specificity for inflammatory sites and infection processes, peptides for having specificity for tumours (for example, somatostatin and derivatives thereof), peptides for having specificity for blood clots and atherosclerotic plaques, cytotoxic agents, monoclonal antibodies and fragments thereof.

Groups of compounds preferred within the scope of the invention comprise compounds having the following general formulae:

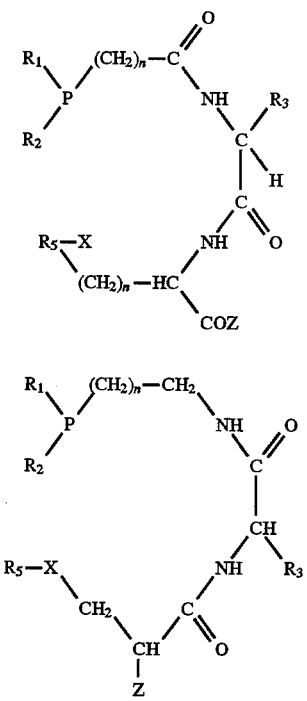

in which n is 1 or 2 and the other symbols have the meanings given above.

From the point of view of the co-ordination around the metal, formulae (II) and (III) are considered as containing the co-ordinating set $PN_2X$ and are constituted by the phosphine group and a dipeptide condensed by means of a peptide or amide bond.

Compounds of the general formula (IV) and (V) are also included within the scope of the invention:

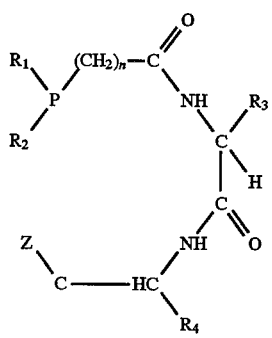

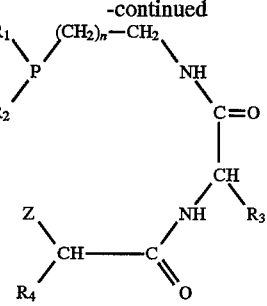

in which Z is amino or a peptide useful for diagnosis, radiotherapy or NMR, connected by means of its N-terminal group (NH-peptide), and in which the co-ordinating set is $PN_3$.

Another general formula within the scope of the invention is that in which the phosphine group is bonded to the carboxyl group of aspartic acid (VI):

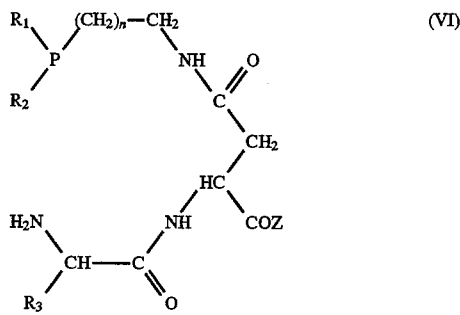

in which Z is $NH_2$ or NH-peptide.

Formula (VI) may be used to bond a second phosphine group $-PR_1R_2$ to the $-NH_2$ terminal and thus to form the co-ordinating set $P_2N_3$ (general structural formula VII):

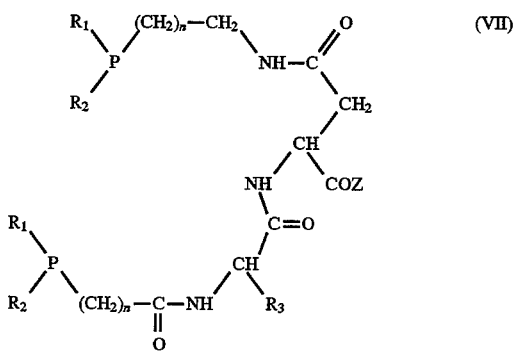

Molecules which use the co-ordinating set $P_2N_2$, obtained by bonding two phosphine groups to a single amino-acid having the general formula (VIII) are also included:

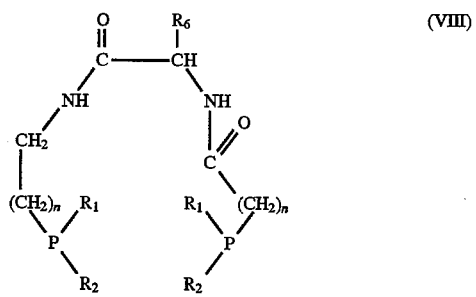

The modification of the peptides with a phosphine group can be carried out with the use of the normal "coupling" reaction (see, in the literature, M. Bodansky, A. Bodansky; "The Practice of Peptide Synthesis", Springer Verlag, New York, 1984 - bibliographical reference (1)), for example, by means of reactions which can be shown schematically as follows:

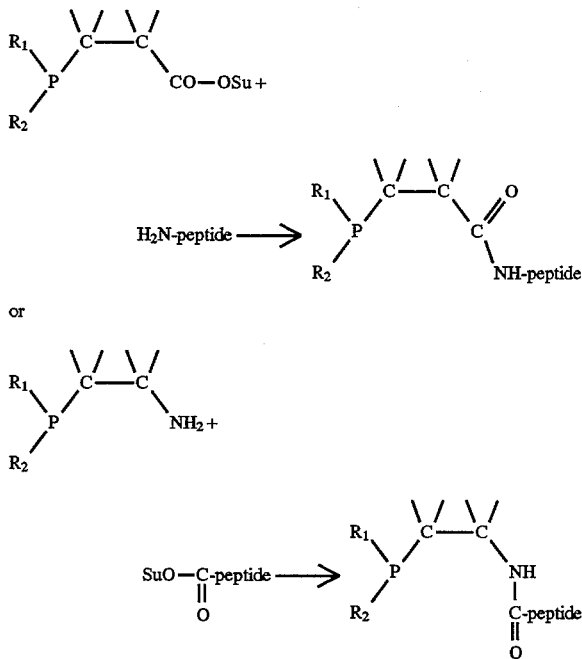

in which Su is the succinimide radical. For the reaction conditions see bibliographical reference (1).

The modification can also be achieved by other reactions such as:

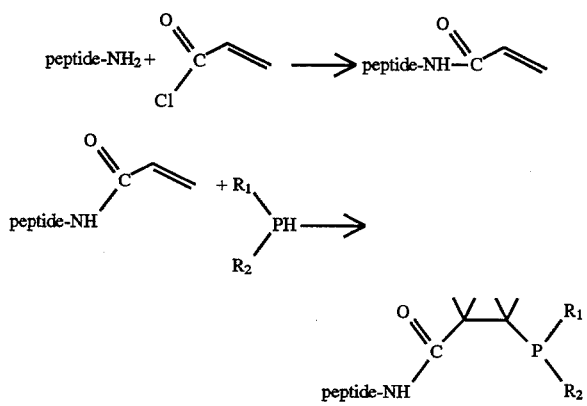

These molecules are synthesized in order to mark protein or peptide substances with radioactive or paramagnetic metals and thus to be able to follow their behaviour in vivo and thereby to establish a clinical diagnosis or to carry out radiotherapy.

In particular, the molecules according to the invention are useful for bonding $^{99m}$Tc and $^{186-188}$Re, preferably with an oxidation state of +5. Lower oxidation states can only be achieved in some cases.

Paramagnetic agents which can be bonded preferably comprise gadolinium or iron.

Complexes comprising Re, Tc or the aforementioned paramagnetic agents, as well as the use of these complexes for diagnosis, radiotherapy and magnetic resonance applications are intended to fall within the scope of the invention.

EXAMPLE 1

Synthesis of $Ph_2P(CH_2)_2CONH$-gly-cys-(Bzl)COOMe.

BOC-gly, Hcys(Bzl)COOMe.HCl and $Ph_2P(CH_2)_2COOH$ were obtained commercially.

A. Preparation of BOC-gly-OSu (bibl. ref. (1)):

1.72 g (10 mmoles) of BOC-gly were dissolved in 170 ml of methylene chloride; 1.28 g (12 mmoles) of N-hydroxysuccinimide were added thereto. After stirring for five minutes in a bath at 0° C., 2.5 g (12 mmoles) of dicyclohexylcarbo-diimide were added. The reaction mixture was left for twelve hours at 4° C. with stirring. The precipitate of decyclohexyl urea was filtered out and the solution was brought to dryness on a rotavapor. The pure product was obtained by recrystallization from isopropanol (yield 75%).

B. Synthesis of Hgly.cys(Bzl)COOMe (bibl. ref.(1)):

3.7 g (14 mmoles) of Hcys(Bzl)COOMe.HCl were placed in anhydrous methylene chloride (50 ml) with $Et_3N$ (2.1 ml, 15 mmoles) and stirred for ten minutes. A solution of BOCglyCOOSu (3.9 g, 14 mm) in 100 ml of anhydrous methylene chloride was then added to this mixture. The reaction was followed by TLC. Upon completion of the reaction (several hours) the impurities were eliminated by successive extractions with 1) 10M HCl, 2) 5% $NaHCO_3$, 3) $H_2O$. A yellowish oil was obtained by evaporation (yield 94%). The BOC was deprotected with trifluoroacetic acid. The product was recovered by evaporation of the acid on a rotavapor and then with an oil pump. The oily product was transformed into the hydrochloride by alcoholic solution saturated with HCl and was precipitated with ethyl ether (yield 93%).

C. Synthesis of $Ph_2P(CH_2)_2COOSu$:

The carboxyl group of the phosphine was activated with an activated ester in an inert atmosphere (argon) to prevent oxidation of the phosphine group to phosphine oxide.

2.58 g (10 mmoles) of $Ph_2P(CH_2)_2COOH$ were placed in 100 ml of anhydrous dioxane and degassed with argon. 1.38 g (12 mmoles) of N-hydroxysuccinimide were added thereto. After a few minutes with stirring, 2.5 g (12 mmoles) of dicyclohexylcarbo-diimide (DCC) were added to the mixture. The white precipitate of dicyclohexyl urea was filtered out and the solution was brought to a small volume by a rotavapor. A white powder was obtained and could be washed with small quantities of anhydrous methanol under argon (yield 65%).

D. Synthesis of $Ph_2P(CH_2)_2CONH$-gly-cys(Bzl)COOMe (L): coupling reaction between Hgly-cys(Bzl)COOMe and $Ph_2P(CH_2)_2COOSu$.

Hgly-cys(Bzl)COOMe.HCl (1.9 g, 6 mmoles) was dissolved in anhydrous dioxane and degassed with argon. 0.91 ml (6.5 mmoles) of $Et_3N$ were added to the mixture. The white triethylamine hydrochloride was eliminated by filtration. 2.14 g of $Ph_2P(CH_2)_2COOSu$, equal to 6 mmoles, were added to the degassed solution and the mixture was left with stirring. The reaction was checked by TLC. Upon completion of the reaction, the solvent was eliminated by evaporation.

The oil obtained was dissolved in ethyl acetate and the impurities were eliminated by extraction with water degassed with argon. After dehydration, the dioxane was eliminated by evaporation. The product was recrystallized with ethyl acetate-petroleum ether (yield 76%). The presence of about 5% of phosphine oxide was confirmed by means of the $^{31}$P NMR spectrum.

Formula of the product obtained:

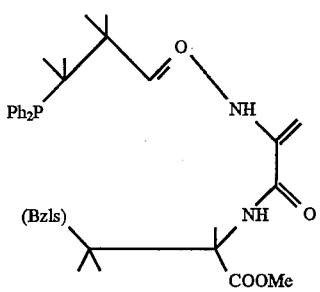

The co-ordinating set in this case is PN$_2$S.

Example of application

Tests for co-ordination and for marking with $^{99m}$Tc were carried out on this ligand.

The co-ordination tests carried out with rhenium led to the identification of two species which contained the ligand intact and which were assumed to contain the molecule in the equatorial plane relative to the ReO$^{3+}$ group.

Reaction:

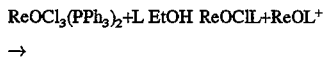

Structure:

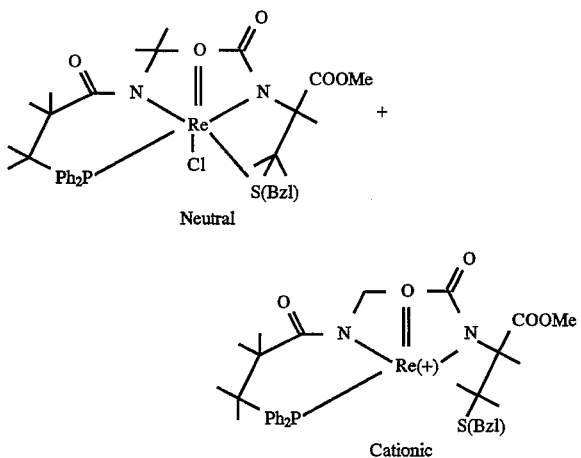

This shows that the thioether group also permits co-ordination. The thiol group can be deprotected with a consequent variation of the co-ordinating capacity of the ligand.

The first results of the $^{99m}$Tc marking tests of the same molecule led to a yield of up to 85% with the use of the pair of reducing agents Sn(tartrate) and NaBH$_4$. These conditions indicate that NaBH$_4$ can deprotect the thiol group of cysteine and lead to good marking. The marking yield will improve if a protector group suitable for deprotection in the marking conditions is used on the cysteine thiol. Other results indicate that very high marking yields can be achieved even in mild conditions (only SnCl$_2$ as the reducing agent); this indicates that a stable technetium complex can be formed even if the ligand contains ethereal sulphur or if there is no deprotection of the cysteine thiol.

From the results obtained, moreover, the possibility of co-ordinating the carboxyl group in place of the thiol group cannot be excluded; in this case, the complex becomes:

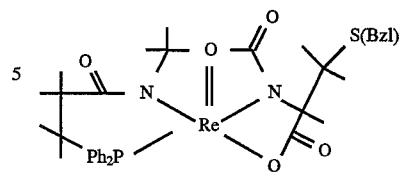

Following the synthesis method described in Example 1, it is possible to prepare the molecules given by way of example in Table 1, which conform to the general formula:

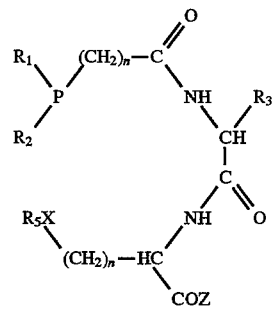

in which n is 1 or 2 and Z is COOH, COOMe or a peptide having useful biological properties, as defined above and in which $R_1$, $R_2$, $R_3$ and $R_5$ have the meanings given in Table 1.

TABLE 1

| Es | X | $R_1$ | $R_2$ | $R_5$ | $R_3$ |
|---|---|---|---|---|---|
| 2 | S$^-$ | $C_6H_5$ | $C_6H_5$ | $C_6H_5CH_2$ | H |
| 3 | S$^-$ | $C_6H_5$ | $C_6H_5$ | $C(C_6H_5)_3$ | H |
| 4 | S$^-$ | $C_6H_5$ | $C_6H_5$ | $C_6H_5CH_2$ | $CH_3$ |
| 5 | S$^-$ | $C_6H_5$ | $C_6H_5$ | $C(C_6H_5)_3$ | $CH_3$ |
| 5a | S$^-$ | $C_2H_5$ | $C_2H_5$ | $C_6H_5CH_2$ | H |
| 6 | S$^-$ | $C_2H_5$ | $C_2H_5$ | $C(C_6H_5)_3$ | H |
| 7 | S$^-$ | $C_2H_5$ | $C_2H_5$ | $C_6H_5CH_2$ | $CH_3$ |
| 8 | S$^-$ | $C_2H_5$ | $C_2H_5$ | $C(C_6H_5)_3$ | $CH_3$ |
| 9 | S$^-$ | $C_6H_5$ | $C_6H_5$ | $C_6H_5CH_2$ | $CH(CH_3)_2$ |
| 10 | S$^-$ | $C_6H_5$ | $C_6H_5$ | $C(C_6H_5)_3$ | $CH(CH_3)_2$ |
| 11 | S$^-$ | $C_6H_5$ | $C_6H_5$ | $C_6H_5CH_2$ | $CH_2CH(CH_3)_2$ |
| 12 | S$^-$ | $C_6H_5$ | $C_6H_5$ | $C(C_6H_5)_3$ | $CH_2CH(CH_3)_2$ |
| 13 | S$^-$ | $C_2H_5$ | $C_2H_5$ | $C_6H_5CH_2$ | $CH(CH_3)_2$ |
| 14 | S$^-$ | $C_2H_5$ | $C_2H_5$ | $C(C_6H_5)_3$ | $CH(CH_3)_2$ |
| 15 | S$^-$ | $C_2H_5$ | $C_2H_5$ | $C_6H_5CH_2$ | $CH_2CH(CH_3)_2$ |
| 16 | S$^-$ | $C_2H_5$ | $C_2H_5$ | $C(C_6H_5)_3$ | $CH_2CH(CH_3)_2$ |
| 17 | S$^-$ | $C_6H_5$ | $C_6H_5$ | $C_6H_5CH_2$ | $CH_2C_6H_5$ |
| 18 | S$^-$ | $C_6H_5$ | $C_6H_5$ | $C(C_6H_5)_3$ | $CH_2C_6H_5$ |
| 19 | S$^-$ | $C_6H_5$ | $C_6H_5$ | $C_6H_5CH_2$ | $(CH_2)_2SCH_3$ |
| 20 | S$^-$ | $C_6H_5$ | $C_6H_5$ | $C(C_6H_5)_3$ | $(CH_2)_2SCH_3$ |
| 21 | S$^-$ | $C_2H_5$ | $C_2H_5$ | $C_6H_5CH_2$ | $CH_2C_6H_5$ |
| 22 | S$^-$ | $C_2H_5$ | $C_2H_5$ | $C(C_6H_5)_3$ | $CH_2C_6H_5$ |
| 23 | S$^-$ | $C_2H_5$ | $C_2H_5$ | $C_6H_5CH_2$ | $(CH_2)_2SCH_3$ |
| 24 | S$^-$ | $C_2H_5$ | $C_2H_5$ | $C(C_6H_5)_3$ | $(CH_2)_2SCH_3$ |
| 25 | S$^-$ | $C_6H_5$ | $C_6H_5$ | $C_6H_5CH_2$ | $(CH_2)_4NH_2$ |
| 26 | S$^-$ | $C_6H_5$ | $C_6H_5$ | $C(C_6H_5)_3$ | $(CH_2)_4NH_2$ |
| 27 | S$^-$ | $C_6H_5$ | $C_6H_5$ | $C_6H_5CH_2$ | $CH_2OH$ |
| 28 | S$^-$ | $C_6H_5$ | $C_6H_5$ | $C(C_6H_5)_3$ | $CH_2OH$ |
| 29 | S$^-$ | $C_2H_5$ | $C_2H_5$ | $C_6H_5CH_2$ | $(CH_2)_4NH_2$ |
| 30 | S$^-$ | $C_2H_5$ | $C_2H_5$ | $C(C_6H_5)_3$ | $(CH_2)_4NH_2$ |
| 31 | S$^-$ | $C_2H_5$ | $C_2H_5$ | $C_6H_5CH_2$ | $CH_2OH$ |
| 32 | S$^-$ | $C_2H_5$ | $C_2H_5$ | $C(C_6H_5)_3$ | $CH_2OH$ |
| 33 | S$^-$ | $C_6H_5$ | $C_6H_5$ | $C_6H_5CH_2$ | $CH_2CONH_2$ |
| 34 | S$^-$ | $C_6H_5$ | $C_6H_5$ | $C(C_6H_5)_3$ | $CH_2CONH_2$ |
| 35 | S$^-$ | $C_6H_5$ | $C_6H_5$ | $C_6H_5CH_2$ | $(CH_2)_2CONH_2$ |
| 36 | S$^-$ | $C_6H_5$ | $C_6H_5$ | $C(C_6H_5)_3$ | $(CH_2)_2CONH_2$ |
| 37 | S$^-$ | $C_2H_5$ | $C_2H_5$ | $C_6H_5CH_2$ | $CH_2CONH_2$ |
| 38 | S$^-$ | $C_2H_5$ | $C_2H_5$ | $C(C_6H_5)_3$ | $CH_2CONH_2$ |
| 39 | S$^-$ | $C_2H_5$ | $C_2H_5$ | $C_6H_5CH_2$ | $(CH_2)_2CONH_2$ |

TABLE 1-continued

| Es | X | R₁ | R₂ | R₅ | R₃ |
|---|---|---|---|---|---|
| 40 | S⁻ | C₂H₅ | C₂H₅ | C(C₆H₅)₃ | (CH₂)₂CONH₂ |
| 41 | O⁻ | C₆H₅ | C₆H₅ | H | H |
| 42 | O⁻ | C₆H₅ | C₆H₅ | H | CH₃ |
| 43 | O⁻ | C₂H₅ | C₂H₅ | H | H |
| 44 | O⁻ | C₂H₅ | C₂H₅ | H | CH₃ |
| 45 | O⁻ | C₆H₅ | C₆H₅ | H | CH(CH₃)₂ |
| 46 | O⁻ | C₆H₅ | C₆H₅ | H | CH₂CH(CH₃)₂ |
| 47 | O⁻ | C₂H₅ | C₂H₅ | H | CH(CH₃)₂ |
| 48 | O⁻ | C₂H₅ | C₂H₅ | H | CH₂CH(CH₃)₂ |
| 49 | O⁻ | C₆H₅ | C₆H₅ | H | CH₂C₆H₅ |
| 50 | O⁻ | C₆H₅ | C₆H₅ | H | (CH₂)₂SCH₃ |
| 51 | O⁻ | C₂H₅ | C₂H₅ | H | CH₂C₆H₅ |
| 52 | O⁻ | C₂H₅ | C₂H₅ | H | (CH₂)₂SCH₃ |
| 53 | O⁻ | C₆H₅ | C₆H₅ | H | (CH₂)₄NH₂ |
| 54 | O⁻ | C₆H₅ | C₆H₅ | H | CH₂OH |
| 55 | O⁻ | C₂H₅ | C₂H₅ | H | (CH₂)₄NH₂ |

What is claimed is:

1. Chelating compounds having the following general structural formula:

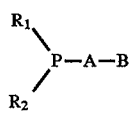  (I)

in which R₁ and R₂ are selected independently from the group consisting of:

H, linear or branched $C_1$-$C_5$ alkyl, linear or branched substituted $C_1$-$C_5$ alkyl, OH, $C_1$-$C_5$ alkoxy, phenoxy, and substituted phenyl groups, and in which A is alkylene carbonyl or alkylene amino in which the alkylene has from 1 to 4 carbon atoms and may be linear or branched, and in which, when A is alkylene carbonyl, B is:

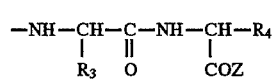

in which R₃ is a group selected from the radicals constituting the lateral chain of a natural amino-acid;

R₄ is selected from the group consisting of:

H, linear or branched $C_1$-$C_4$ alkyl groups, —CH₂—C₆H₅, —(CH₂)ᵣNH₂ where r is an integer from 1 to 4, —(CH₂)ₚ—CONH₂ where p is an integer from 1 to 3, —(CH₂)ₙXR₅ where n is 1 or 2 and X is selected from —O⁻, —S⁻, and —COO⁻, and R₅ is H or a protector group;

Z is OH, OMe, NH₂ or is the same as R₄, or Z is a peptide with biological properties useful for diagnosis, radiotherapy or magnetic resonance, bonded to the preceding carbon atom by means of its N-terminal group;

and in which, when A is alkylene amino, B is selected from the group consisting of:

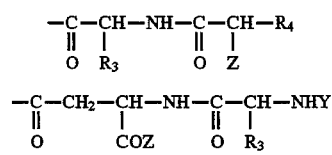

and

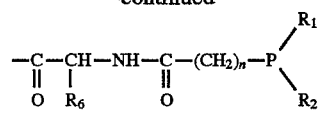

where R₁, R₂, R₃, R₄, n and Z have the meanings given above and R₆ has the same meaning as R₃ given above, or has the meaning of Z given above, and Y is H or

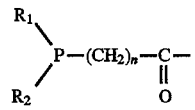

where R₁, R₂ and n have the meanings given above.

2. Compounds according to claim 1 in which R₁ and R₂ in formula (I) are substituted alkyl, the substituents are hydroxyl, ether, ester, amide, ketone, aldehyde or nitrile groups.

3. Compounds according to claim 1 in which, when R₁ and R₂ in formula (I) are substituted phenyl, the substituents are selected from hydroxyl, ketone, nitrile, ether (—O—$C_1$-$C_5$), ester and amide groups.

4. Compounds according to claim 1, in which, when X is —S⁻, the protector groups R₅ at X are selected from $C_1$-$C_5$ alkyl, phenyl, and substituted benzoyl groups.

5. Compounds according to claim 1 in which the protector groups are selected from the group consisting of terbutyl, methoxymethyl, 2-tetrahydropyranyl, benzyl, 3,4-dimethylbenzyl, p-methoxybenzyl, p-hydroxy-o-acetoxybenzyl, benzylthiomethyl, p-nitrobenzyl, diphenylmethyl, bis(4-methoxyphenyl)methyl, phenyl, 2,4-dinitrophenyl, acetylbenzoyl, thiobenzoyl, butoxycarbonyl, benzyloxycarbonyl, and N-methoxymethyl groups.

6. Compounds according to claim 1 in which, when X is COO⁻, R₅ is a linear or branched $C_1$-$C_5$ alkyl group or a $C_1$-$C_5$ alkyl group substituted with $C_1$-$C_5$ alkylester or arylester groups.

7. Compounds according to claim 1, in which, when X is O, R₅ is selected from the group consisting of $C_1$-$C_5$ alkyl, aryl, $C_1$-$C_5$ alkylcarbonyl and arylcarbonyl.

8. Compounds according to claim 1, in which R₅ is selected from the group consisting of acetyl, phenyl, benzyl, terbutyl, methyl, benzyloxycarbonyl, BOC, 1-benzyloxycarbonylamino-2,2,2-trifluoroacetyl, and o-trialkylsilyl groups.

9. Compounds according to claim 1 wherein, Z is a molecule with biological properties useful for diagnosis, radiotherapy or magnetic resonance, and is selected from avidin, biotin, low-density lipoprotein (LDL), chemotactic peptides having specificity for inflammatory sites and infection processes, peptides having specificity for tumours, peptides having specificity for blood clots and atherosclerotic plaques, cytotoxic agents, monoclonal antibodies and fragments thereof.

10. Compounds according to claim 1, having a co-ordinating set PN₂X according to the following general formulae (II) or (III):

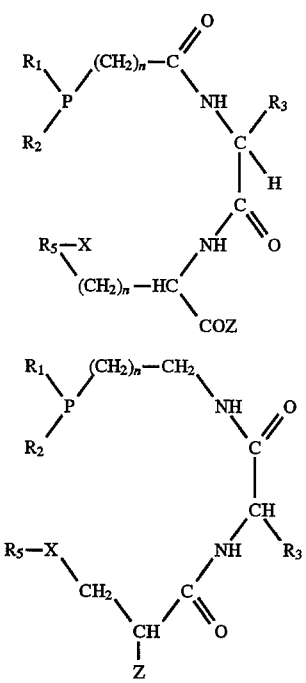
(II)

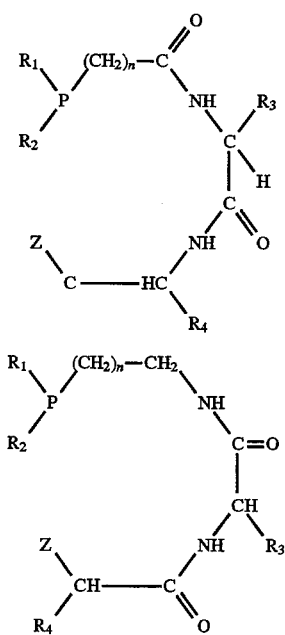
(III)

in which n is 1 or 2 and the other symbols have the meanings given above.

11. Compounds according to claim 1, having a co-ordinating set $PN_3$, of the general formula (IV) and (V):

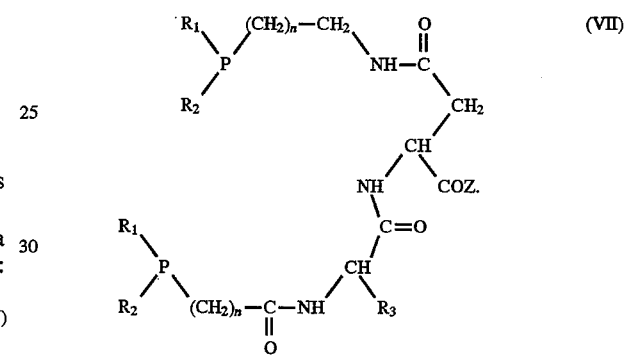
(IV)

(V)

in which Z is amino or a peptide useful for diagnosis, radiotherapy or NMR, connected by means of its N-terminal.

12. Compounds according to claim 1 in which the phosphine group is bonded to the carboxyl group of aspartic acid of the general formula (VI):

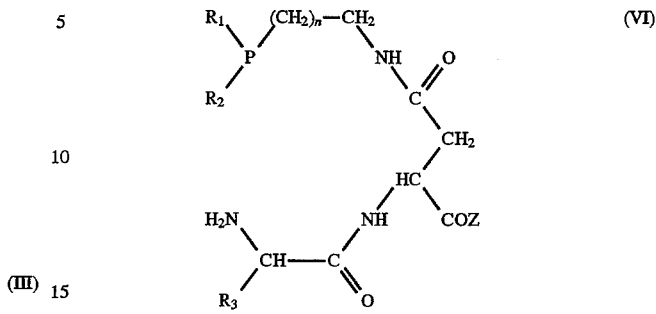
(VI)

in which Z is $NH_2$ or NH-peptide.

13. Compounds according to claim 1, having a co-ordinating set $P_2N_3$, with the general structural formula VII:

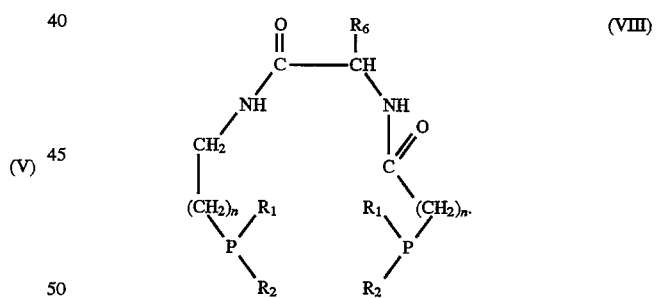
(VII)

14. Compounds according to claim 1 having the co-ordinating set $P_2N_2$, obtained by bonding two phosphine groups to a single amino-acid, having the general formula (VIII):

(VIII)

15. Compounds according to claim 1, in which, the linear or branched $C_1$–$C_4$ alkyl $R_4$ groups are methyl, ethyl, isopropyl or 2-methylpropyl.

16. Compounds according to claim 2, in which, the ether substituents are $C_1$–$C_5$ alkoxy.

17. Compounds according to claim 2, in which, the ester substituents are $C_1$–$C_5$COO—.

* * * * *